US012728031B2

(12) United States Patent
Basson

(10) Patent No.: US 12,728,031 B2
(45) Date of Patent: Sep. 8, 2026

(54) DEVICE FOR INSERTION INTO A VAGINA

(71) Applicant: Johannes Basson, Enfield (GB)

(72) Inventor: Johannes Basson, Enfield (GB)

( * ) Notice: Subject to any disclaimer, the term of this patent is extended or adjusted under 35 U.S.C. 154(b) by 659 days.

(21) Appl. No.: 18/252,289

(22) PCT Filed: Nov. 9, 2021

(86) PCT No.: PCT/EP2021/081068
§ 371 (c)(1),
(2) Date: May 9, 2023

(87) PCT Pub. No.: WO2022/101181
PCT Pub. Date: May 19, 2022

(65) Prior Publication Data

US 2023/0404792 A1 Dec. 21, 2023

(30) Foreign Application Priority Data

Nov. 10, 2020 (GB) ..................................... 2017693

(51) Int. Cl.
*A61F 5/455* (2006.01)
*A61F 6/08* (2006.01)
*A61F 5/44* (2006.01)

(52) U.S. Cl.
CPC .............. *A61F 5/4553* (2013.01); *A61F 6/08* (2013.01); *A61F 5/4404* (2013.01); *A61F 5/455* (2013.01)

(58) Field of Classification Search
CPC ...... A61F 5/4553; A61F 5/4404; A61F 5/455; A61F 6/08
See application file for complete search history.

(56) References Cited

U.S. PATENT DOCUMENTS 1,790,801 A * 2/1931 Dickstein ................ A61F 2/005 128/834
2,101,875 A * 12/1937 Schleicher ................ A61F 6/12 128/838
2,310,564 A * 2/1943 Younkins .................. A61F 6/08 128/837
3,102,541 A 9/1963 Adams
(Continued)

FOREIGN PATENT DOCUMENTS

FR 363976 A 8/1906
GB 05103 A * 3/1909 ........... A61F 5/4553

OTHER PUBLICATIONS

International Search Report and Written Opinion for PCT/E P2021/081068 dated Feb. 28, 2022, 15 pages.
(Continued)

*Primary Examiner* — Guy K Townsend
(74) *Attorney, Agent, or Firm* — Kari L Barnes

(57) ABSTRACT

There is herein provided a device (200) for insertion into a vagina. The device comprises a cervical ring (202) configured to surround the cervix, a positioning portion (204) configured to abut against a securing position along an interior wall of the vagina and an elastically resilient connecting portion (206). The elastically resilient connecting portion connects the cervical ring and the positioning portion and the elastically resilient connecting portion is configured such that, when the device is positioned inside the vagina, the positioning portion is biased against the securing position.

18 Claims, 7 Drawing Sheets

(56) References Cited

U.S. PATENT DOCUMENTS

| | | | | |
|---|---|---|---|---|
| 3,791,385 | A * | 2/1974 | Davis | A61F 13/2051 604/12 |
| 4,711,235 | A * | 12/1987 | Willis | A61F 6/08 128/839 |
| 6,168,609 | B1 * | 1/2001 | Kamen | A61F 5/4553 600/573 |
| 6,332,878 | B1 * | 12/2001 | Wray | A61F 5/4556 128/830 |
| 2012/0071709 | A1 * | 3/2012 | Spitz | A61F 2/005 600/30 |
| 2020/0337889 | A1 * | 10/2020 | Brown | A61L 27/165 |
| 2023/0404792 | A1 * | 12/2023 | Basson | A61F 6/08 |

OTHER PUBLICATIONS

Combined Search and Examination Report for GB2017693.9 dated Mar. 29, 2021, 5 pages.

European Search Report for EP 21811266.2, dated Jul. 7, 2025, 5 pages.

* cited by examiner

DEVICE FOR INSERTION INTO A VAGINA

PRIORITY

This application is a National Stage under 35 USC 371 of PCT/EP2021/081068, filed Nov. 9, 2021, claiming priority to Great Britain Patent Application Number 2017693.9, filed Nov. 10, 2020.

FIELD OF THE INVENTION

The present invention relates to a device for insertion into a vagina, and in particular relates to a sanitary device for use during menstruation.

BACKGROUND

Pelvic organ prolapse is when one or more of the organs in the pelvis slips down from its normal position and bulges into the vagina. This can include the uterus, bladder, bowel and/or top of the vagina. Pelvic organ prolapse happens when the group of muscles and tissues that normally support the pelvic organs, called the pelvic floor, becomes weakened and can't hold the organs in place firmly. Pelvic organ prolapse usually occurs when the pelvic floor collapses after gynaecological cancer treatment, childbirth or heavy lifting.

A prolapse isn't life-threatening, but it can cause pain and discomfort. Symptoms can usually be improved with pelvic floor exercises and lifestyle changes, however, in severe cases it is common for surgery to be needed.

A known alternative treatment to therapy is a ring pessary. A conventional ring pessary is a rubber or silicone rubber device fitted to the patient by insertion into the vagina. Such a device may be retained for up to several months. Pessaries are a good choice of treatment for women who wish to maintain fertility, are poor surgical candidates, or who may not be able to attend physical therapy. Pessaries require a provider to fit the device, but most can be removed, cleaned, and replaced by the woman herself. Pessaries are a good choice for treating prolapse, however, they can often become dislodged and move during use. It is therefore desirable to provide a device that can be more securely fitted within the vagina.

Sanitary towels and tampons are the most commonly used sanitary devices currently used during menstruation to absorb blood. It is estimated that the average woman uses 10,000 tampons during her lifetime. Sanitary towels and tampons are typically made from materials such as paper, non-woven fabric, plastic and other chemicals. These materials are only suitable for one use only and cannot be reused. For example, about 90% of the materials used to make sanitary pads and liners are plastic and include materials such as polyethylene, polypropylene and polyacrylate super absorbents. This generates a large amount of waste that is difficult to dispose of. The plastics used can cause severe water pollution and clog drains, creating excessive processing and handling costs, especially in less developed countries with less sophisticated waste disposal systems. It is therefore desirable to have a reusable product to reduce the environmental impact.

Additionally, menstruation can adversely affect women when in certain social situations, for example, when on holiday and during sports activities. The high cost of sanitary products means that they are often difficult to obtain. It is therefore desirable to have a reusable product to allow constant access to sanitary products. A reusable product can be provided at a one-off cost and reduce the need for repurchasing of disposable products such as tampons and sanitary towels.

Menstruation can be messy, unhygienic and lead to infections which, although rare, can be fatal, for example toxic shock syndrome. Toxic shock syndrome is caused by bacterial toxins which are facilitated by the use on menstruation products like tampons when left in the vagina too long. It is therefore desirable to produce a hygienic sanitary device that keeps the walls of the vagina as dry as possible.

One attempt at addressing the issues caused by single use sanitary products is the use of a menstrual cup. Conventional menstrual cups are usually made of flexible medical grade silicone and shaped like a bell with a stem used for removal. The menstrual cup's bell-shaped cup seals against the vaginal wall just below the cervix and prevents blood from leaking onto clothes. Although the menstrual cup is a reusable device, there are several problems associated with this device. For example, the menstrual cup is difficult to insert correctly. It can also be messy and especially during removing when spillages may occur. Additionally, the menstrual cup does not keep the walls of the vagina as dry as is desirable.

There therefore remains a need in the art to provide an improved device for use during menstruation, and in particular a device that addresses at least some of the above-identified disadvantages of current menstruation devices.

SUMMARY

Aspects and features of the present invention are described in the accompanying claims.

The present invention describes a device for insertion into a vagina. The device comprises a cervical ring configured to surround the cervix, a positioning portion configured to abut against a securing position along an interior wall of the vagina, and an elastically resilient connecting portion connecting the cervical ring and the positioning portion. The elastically resilient connecting portion is configured such that, when the device is positioned inside the vagina, the positioning portion is biased against the securing position.

The securing position may correspond to the pubic bone and the positioning portion then biased towards the pubic bone. The securing position may also or optionally correspond to the levator muscles and the positioning portion is biased towards the levator muscles. The securing position could also correspond to the puborectalis muscles.

The device may further include a bag connected to the cervical ring and the bag may further comprises a valve. The bag may be configured to be removable from the cervical ring and the bag may be configured to extend from the cervical ring to the opening of the vagina.

The positioning portion may include a positioning ring comprising a first end and a second end. The first end is configured to abut against the securing position and the second end is configured to abut against a backwall of the vagina. The positioning ring may be elastically resilient, and the first end of the positioning ring is biased against the securing position and the second end of the positioning ring is biased against the backwall of the vagina.

The device may be elastically deformable such that the device may be inserted into the vagina.

The positioning portion may further include an indentation configured to accommodate the urethra when the device is positioned inside the vagina. The device may further include at least one tab protruding from the device.

The cervical ring may further include an inflatable portion. The inflatable portion may be positioned on the circumference of the cervical ring. Further, the inflatable portion may include a first pilot line with a first end connected to the inflatable portion and a second end connected to a first valve. The first pilot line is configured to provide air to inflate the inflatable portion.

The device may further include a washing tube and the washing tube includes a first opening configured to deliver water to the walls of the vagina. The washing tube can be located in the inflatable portion of the device. The washing tube may also be located in the cervical ring or in the wall of the bag. The washing tube may include a second pilot line with a first end connected to the washing tube and a second end connected to a second valve. The second pilot line is configured to deliver water to the washing tube and the first pilot line and second pilot line may be removable. The washing tube can also include a second opening configured to deliver water to the inside of the bag.

The connecting portion may be curved and the gradient of the curve of the connecting portion increases as distance from the cervical ring increases.

The at least one tab can extend downwards such that, when the device is positioned inside the vagina, the at least one tabs extends towards the opening of the vagina. The device may have at least two tabs, and one tab located on each side of the positioning portion such that, when the device is positioned inside the vagina, the device will have one tab located on each side of the pubic bone.

The indentation may be located in the centre of the positioning portion.

The inflatable portion may be configured to inflate from a first volume to a second volume. The second volume is greater than the first volume.

The interior wall of the vagina can be an anterior wall of the vagina.

FIGURES

Specific embodiments are described below by way of example only and with reference to the accompanying drawings in which:

FIG. 1*a* illustrates a cross section of the female pelvis.

FIG. 1*b* illustrates a plan view of the female pelvis.

FIG. 1*c* illustrates a cross section of the female pelvis including a device for insertion into the vagina.

DETAILED DESCRIPTION

Figure 1A:
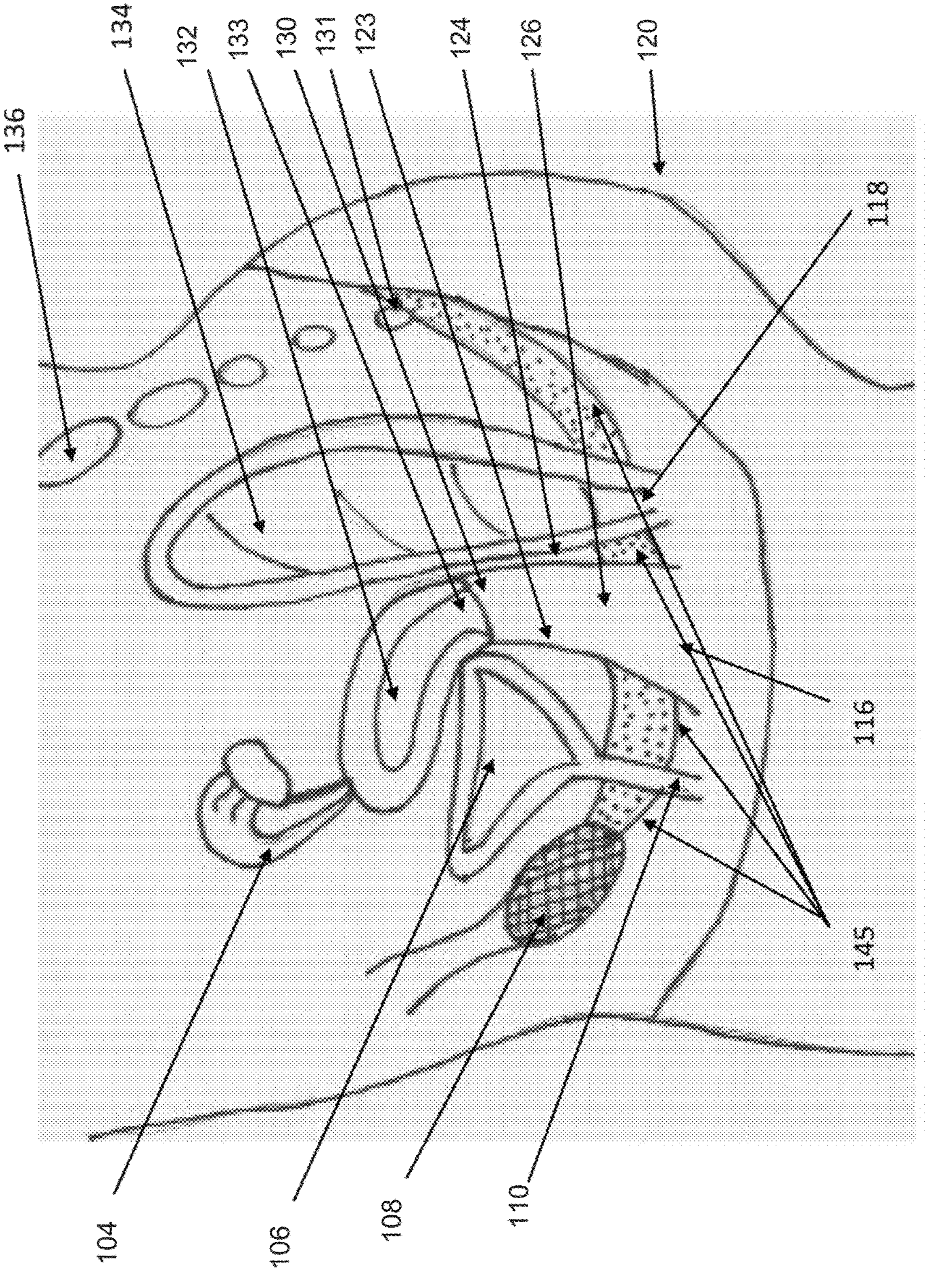

FIG. 1*a* will be briefly discussed to provide background to the invention. FIG. 1*a* shows a cross section of the female pelvis, for perspective the vertebral or spinal column 136 and buttock 120 is shown at the far right of the figure. The pubic bone 108 is located at the anterior (front) of the body. The pubic bone 108 is one of the bones that make up the pelvis and is covered by a layer of fat. The pubic bone 108 is located at the lower anterior of the pelvis in the pubic area, as shown in FIG. 1*a*. The pubic bone 108 helps to connect the two hip bones at the front of the human body at a location called the pubic symphysis (not shown).

Posterior to the pubic bone 108 is the urinary bladder 106. The urinary bladder 106 stores urine, allowing urination to be regulated. The urinary bladder 106 is lined by layers of muscle tissue that stretch to hold urine. Urine exits the urinary bladder 106 into the urethra 110, which carries urine out of the body. The urethra 110 exits the body between the clitoris (not shown) and the vagina 126. The urethra 110 is located adjacent to the vagina 126.

The vagina 126 is located posterior to the urinary bladder 106 and urethra 110 and anterior to the rectum 134. The vagina 126 has an anterior wall 123 and a posterior wall 124. The anterior wall 123 is shorter than the posterior wall 124 and is generally approximately 7.5 cm in length, whereas the posterior wall 124 of the vagina 126 is generally approximately 8.5 cm in length. The vagina 126 is generally directed obliquely upward and backward as compared to a line perpendicular to the floor when a woman is standing straight. The urethra 110 is often pressed into the vagina 126 such that it is embedded in the anterior wall 123 of the vagina 126. The opening of the vagina 116 is located at the bottom of the vagina 126, posterior to the urethra 110 and anterior to the anus 118.

The uterus 132 is located within the pelvic region immediately posterior to the urinary bladder 106, and anterior to the rectum 134. The upper end of the uterus 132 is connected to the fallopian tubes 104, and the lower end of the uterus 132 is connected to the cervix 130. The cervix 130 opens into the vagina 126, projects for a short distance into the vagina 126 and is normally pressed against its posterior wall 124. A central canal, known as the cervical canal 133, runs along the length of the cervix 130 and connects the upper end of the uterus 132 to the vagina 126.

The central axis of the vagina 126 forms an angle with the central axis of the uterus 132. This angle varies considerably from person to person and depending on conditions in the urinary bladder 106, in the rectum 134, and during pregnancy. Typically, this angle is approximately degrees.

Figure 1B:
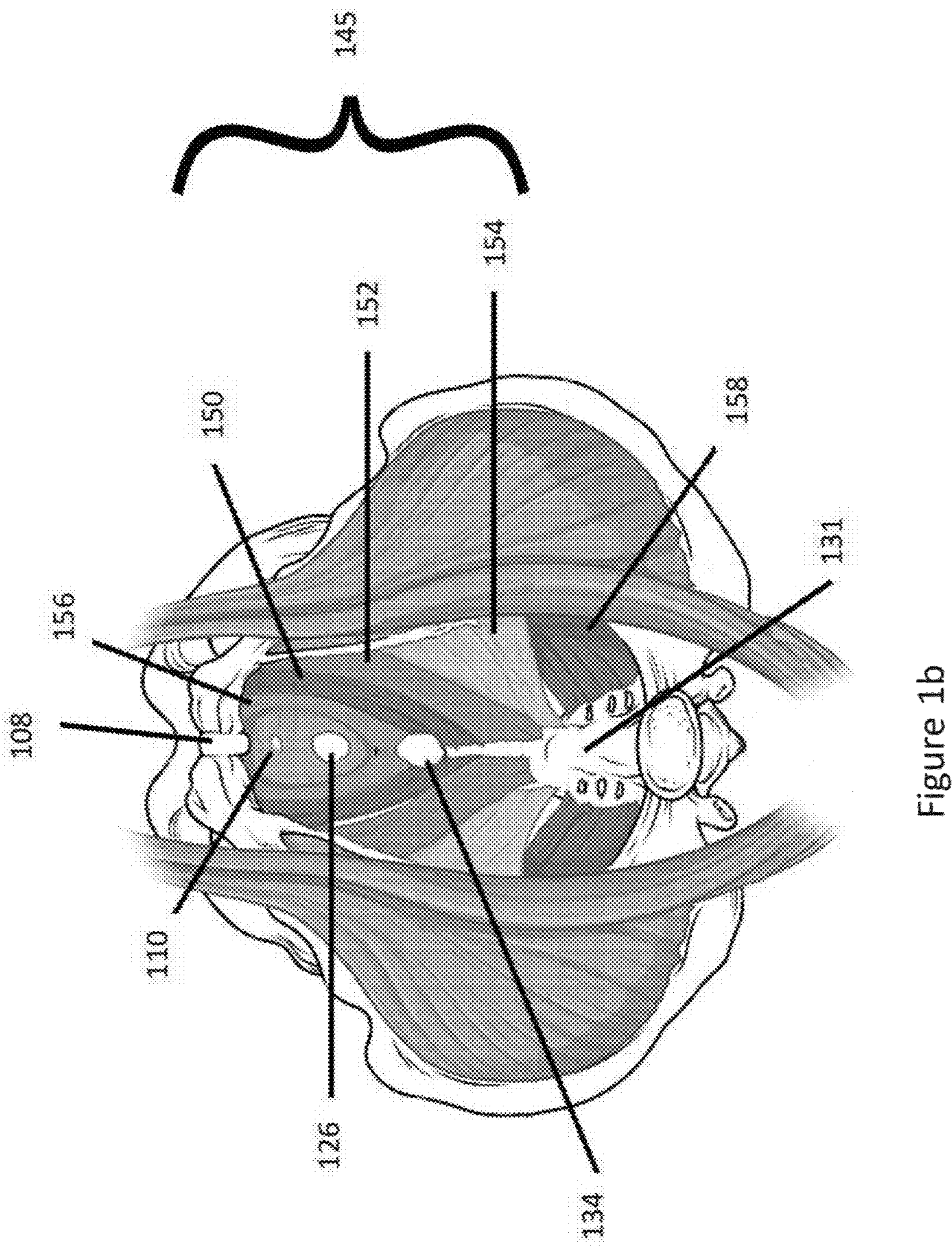

The levator muscles 145 are shown in FIG. 1*a* (indicted by the dotted texture). The levator muscles 145 are a broad, thin muscle group, situated on either side of the pelvis. FIG. 1*b* illustrates a plan view of the female pelvis and the levator muscles 145 are shown in more detail. The levator muscles 145 are formed from three muscle components: the puborectalis 150, the pubococcygeus 152 and the iliococcygeus 154. They are attached to the inner surface of each side of the pelvis, and these unite to form the greater part of the pelvic floor and have the function of supporting the pelvic organs (i.e. bladder, uterus etc). The levator muscles 145 are located in the order puborectalis 150, pubococcygeus 152, iliococcygeus 154 from anterior to posterior.

The puborectalis 150 muscle is a U-shaped sling muscle, extending from the pubic bone 108 around the rectum 134. The main function of this thick muscle is to maintain continence in the rectum 134. Some fibers of the puborectalis muscle 156 (pre-rectal fibers) form another U-shaped sling that flank the urethra 110 and vagina 126. These fibers are very important in preserving urinary continence.

The muscle fibres of the pubococcygeus 152 are the main constituent of the levator muscles 145. They arise from the body of the pubic bone 108 and the anterior aspect of the tendinous arch (not shown). The fibres travel around the outside of the urethra 110 and vagina 126 and attach at the coccyx 131.

The iliococcygeus 154 muscle arises from the inner side of the lower and back part of the hip bone (not shown) and is attached to the coccyx 131. The coccygeus 158 muscle is also shown for reference.

Figure 1C:
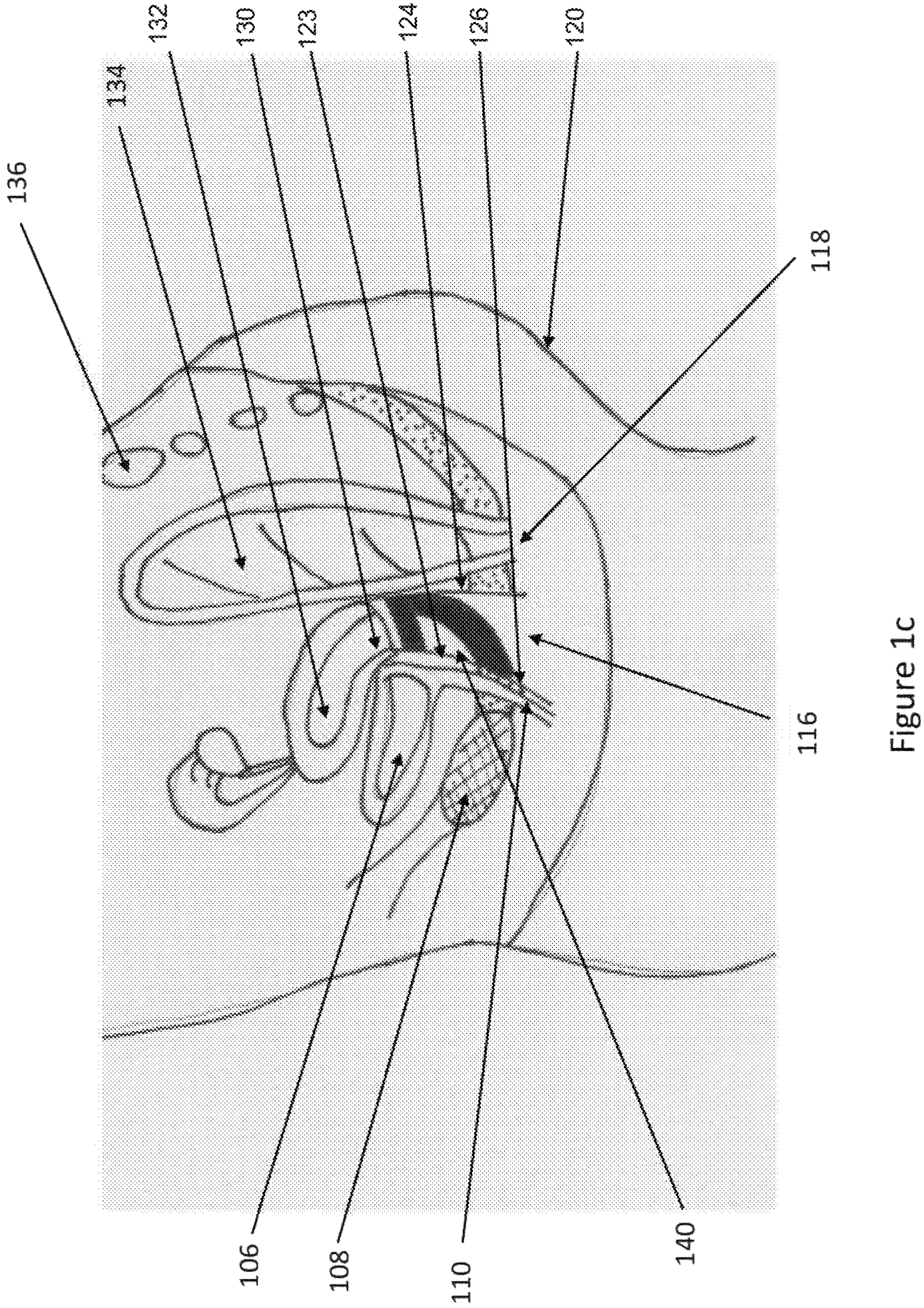

FIG. 1*c* further shows a device 140 for insertion into a vagina 126. The device 140 for insertion into a vagina 126 could, for example, be used as a sanitary device for use during menstruation. Alternative uses of the device 140 include for supporting the vaginal walls 123 and 124 and pelvic organs during pelvic organ prolapse, similar to the treatment provided by a ring pessary.

Figure 2:
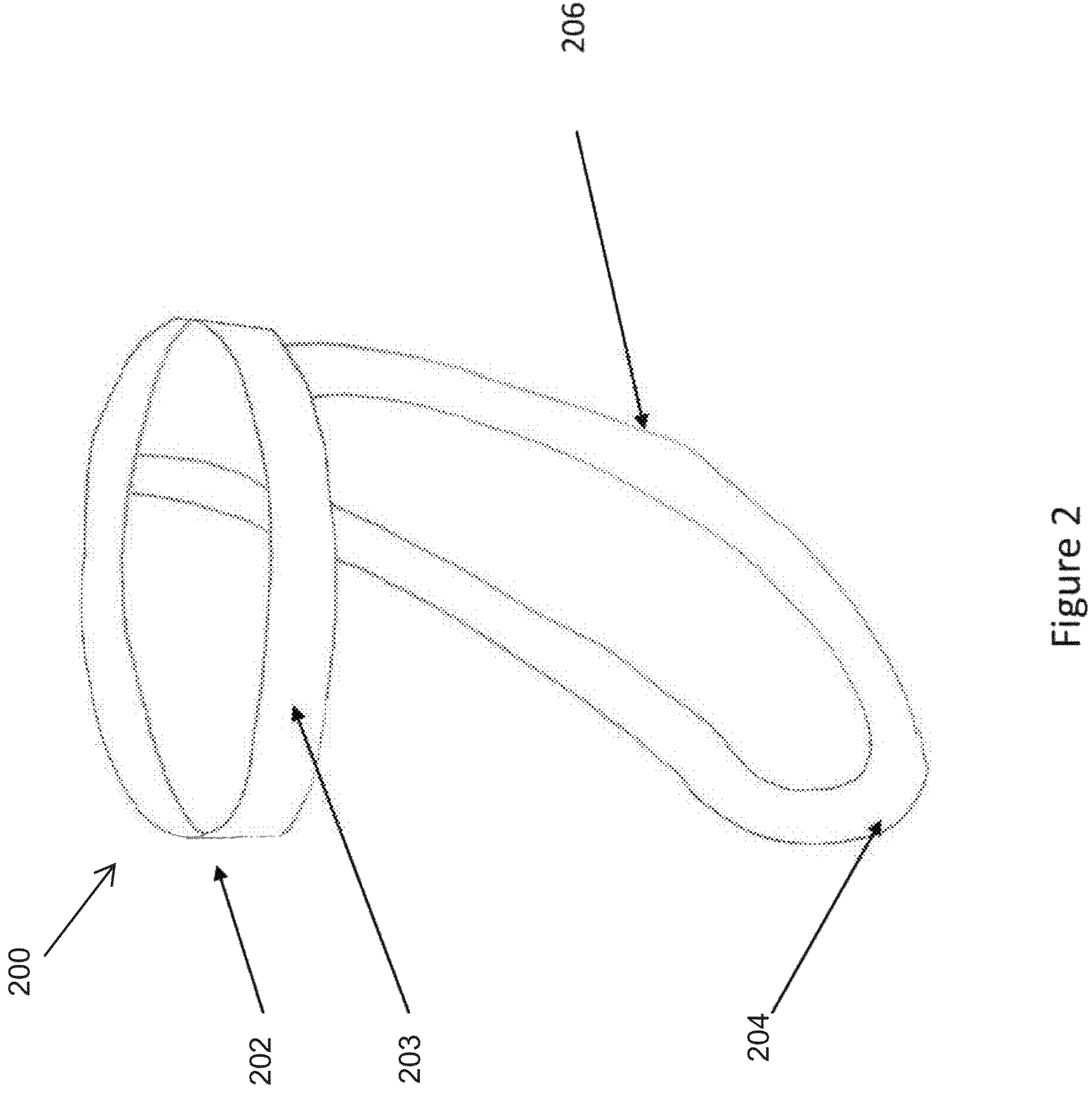
FIG. 2 illustrates a device for insertion into a vagina according to a first aspect of the present disclosure.

FIG. 2 shows a first example of the device 200. As shown in FIG. 2, the device 200 comprises a cervical ring 202, a positioning portion 204 and a connecting portion 206. Each of these sections will now be described in turn.

The cervical ring 202 is located at one end of the device 200 and is a generally loop-shaped section configured to surround the cervix 130 when inserted into the vagina 126. As the cervix 130 of the uterus 132 projects for a short distance into the vagina 126, the cervical ring 202 can be sized and/or shaped such that the cervical ring 202 is configured to surround the cervix 130 completely. When used as a sanitary device for menstruation, the cervical ring 202 surrounds the cervix 130 and ensures that blood discharged from the uterus 132 flows through the cervical ring 202. The cervical ring 202 has a hollow circular shape, or alternatively, the cervical ring 202 can have a hollow ellipse shape. Alternatively, the ring may be doughnut shaped, otherwise known as a torus shape. Indeed, any shape may be used as long as the cervical ring 202 is able to surround the cervix 130 when in use. The cervical ring 202 may be formed of an elastically resilient material such that it may be slightly deformed on insertion or removal from a vagina 126, before elastically returning towards its default shape. The size of the cervical ring 202 may be such that, once inserted into the vagina 126 and surrounding the cervix 130, surfaces of the cervical ring 202 are biased outwards and towards the interior walls (anterior wall, posterior wall and side walls) of the vagina 126. For example, a first part of the cervical ring 202 may be biased towards the anterior wall 123 of the vagina 126 and/or a second part of the cervical ring may be biased towards the posterior wall 124 of the vagina 126. In this manner, the cervical ring 202 is able to provide a retention force against the walls of the vagina 126, thereby aiding in retaining the device within the vagina 126.

Extending from the cervical ring 202 is the connecting portion 206. The connecting portion 206 is connected to, and extends from, the cervical ring 202 as shown in FIG. 2. The connecting portion 206 may extend from any point on the cervical ring 202. For example, when the cervical ring 202 has an ellipse shape, the connecting portion 206 may be located at the vertex or co-vertex or anywhere else along the circumference/edge of the ellipse. When the cervical ring 202 has a circular shape, the connecting portion 206 may be located anywhere along the circumference of the circle. The connecting portion 206 may only extend from the cervical ring 202 at a single point (not shown), or the connecting portion 206 may extend from the cervical ring 202 from two points as shown in FIG. 2.

The connecting portion 206 is also formed of an elastically resilient material so that it has the ability to resist a distorting influence and to return to its original size and shape when that influence or force is removed. The connecting portion 206 may also be generally loop-shaped, as shown in FIG. 2. For example, two ends of the loop-shaped connecting portion 206 may each extend from a different connection point along the circumference of the cervical ring 202. The connecting portion 206 extends generally downward from the cervical ring 202, as compared to a woman standing up straight. The connecting portion 206 is however biased towards an anterior position, i.e. towards the pubic bone and/or levator muscles, such that an angle between the plane of the cervical ring 202 and each end of the loop-shaped connecting portion 206 is less than 90 degrees. It can therefore be seen that the connecting portion 206 does not extend straight down from the cervical ring 202 for at least some of its length, and instead extends generally towards an anterior wall of the vagina 126. The connecting portion 206 can bend towards the anterior wall of the vagina 126 in a smooth curve (see FIG. 2) or a step-change configuration (not shown, i.e. a gradient that changes at intervals). For example, in another embodiment the connecting portion 206 could first extend straight down perpendicularly from the cervical ring 202 or even away from the anterior wall of the vagina 126 (i.e. at 90 degrees or greater) and, after a certain length, curve or bend towards the anterior wall of the vagina 126. As shown in FIG. 2, the connection points that connect the cervical ring 202 to the connecting portion 206 may be located generally at a posterior region of the cervical ring 202, and the connecting portion 206 may extend towards an anterior region of the vagina 126.

Optionally, the connecting portion 206 may be curved. The gradient of the curve of the connecting portion 206 increases as distance from the cervical ring 202 increases. The gradient of the curve of the connecting portion 206 is greatest at the point where the connecting portion 206 joins the cervical ring 202, and the gradient of the curve is least where the connecting portion 206 forms the positioning portion 204.

Although the connecting portion 206 of FIG. 2 is shown as loop-shaped, the connecting portion 206 may only connect to the cervical ring 202 at one point and may therefore be any other shape that extends from posterior to anterior within the vagina 126.

At an opposite end of the device 200, an end region of the connecting portion 206 provides the positioning portion 204. The connecting portion 206 extends in an anterior direction towards the pubic bone and levator muscles 145. The positioning portion 204 is configured to lie against or in a securing position along the anterior wall 123 of the vagina 126.

The exact location of the securing position depends on the specific anatomy of the user. The positioning portion 204 may be configured to abut against a location of the anterior wall 123 that, when the device is inserted, itself abuts against the levator muscles 145 (in particular, the anterior levator muscles) due to a biasing force from the connecting portion 206. In this case, the securing position is the location along the anterior wall 123 that abuts against the levator muscles 145. In other words, the securing position corresponds to the levator muscles 145. The positioning portion 204 can also or instead be configured to abut against a location of the anterior wall 123 that, when the device is inserted, itself abuts the pubic bone 108 due to a biasing force from the connecting portion 206. In this case, the securing position is the location along the anterior wall 123 that abuts the pubic bone 108. In other words, the securing position corresponds to the pubic bone 108. The positioning portion 204 may therefore be located at a securing position that, when the device 200 is inserted into the vagina 126, either lies on the levator muscles 145 or against the pubic bone 108. In other words, the securing position may correspond to one of the levator muscles 145 or the public bone 108.

Alternatively, the securing position along the anterior wall 123 of the vagina 126 may be a location that, when the device 200 is inserted into the vagina 126, abuts against both the levator muscles 145 and against the pubic bone 108 at the same time, since both the levator muscles 145 and pubic bone 108 are located adjacent to each other. In other words, the securing position may correspond to both the levator muscles 145 and the pubic bone 108. The exact location of the positioning portion 204 and securing position when inserted into the vagina 126 will depend on the particular anatomy of the user. Therefore, an advantage of the present device 200 is that it may be adapted to be secured against the pubic bone 108 and/or the levator muscles 145 depending on the best fit for the user of the device 200.

When the securing position corresponds to the levator muscles 145, the positioning portion 204 is biased towards the levator muscles 145. Tissue surrounding the vagina 126 may be compressed to allow the positioning portion 204 to cause the securing position to be on the top of the levator muscles 145 by manually locating the positioning portion 204 at the appropriate point along the anterior wall 123 of the vagina 126. The securing position is therefore biased to lie on top of the anterior levator muscles 145 and the positioning portion 204 is held in place by the strength of the levator muscles 145 and the resilience of the connecting portion 206. More specifically, the securing position will be on the anterior part of the puborectalis 145 muscles but may optionally also make contact with the pubococcygeus 152 muscles as well.

Due to the resilience and shape of the connecting portion 206, once the device 200 is appropriately located within the vagina 126 (cervical ring 202 located around the cervix 130, and positioning portion 204 abutting against the securing position), the connecting portion 206 provides a biasing force to bias both the positioning portion 204 down towards the top of the levator muscles 145, and the cervical ring 202 up against the uterus 132 to surround the cervix 130. This biasing force ensures that the device 200 is securely held within the vagina 126.

When the securing position corresponds to the pubic bone 108, the positioning portion 204 is biased towards the pubic bone 108. There are, however, other organs and tissue located between the positioning portion 204 and the pubic bone 108, including the urethra 110. As such organ/tissue is softer than the pubic bone 108, the tissue may be compressed to allow the positioning portion 204 to bias the securing position against the pubic bone 108 by manually locating the positioning portion 204 at the appropriate point along the anterior wall of the vagina 126. Specifically, the securing position is against the superior surface of pubic bone 108 since, when inserted into the vagina 126, the device 200 is located above the pubic bone 108 and the positioning portion 204 is biased towards the pubic bone 108 from above.

Similarly, due to the resilience and shape of the connecting portion 206, once the device 200 is appropriately located within the vagina 126 (cervical ring 202 located around the cervix 130, and positioning portion 204 abutting against the securing position), the connecting portion 206 provides a biasing force to bias both the positioning portion 204 down towards the superior surface of the pubic bone 108, and the cervical ring 202 up against the uterus 132 to surround the cervix 130. This biasing force ensures that the device 200 is securely held within the vagina 126.

When the securing position corresponds to both the levator muscles 145 and the pubic bone 108, the positioning portion 204 is simultaneously biased towards both the levator muscles 145 and the pubic bone 108. In this case the securing position is on the top of the levator muscles 145 and against the superior surface of the pubic bone 108. The previously described mechanisms simultaneously act together to hold the device 200 in position.

Insertion of the device 200 into the vagina 126 is a simple process. First, the cervical ring 202 is inserted to surround the cervix 130 such that the connecting portion 206 extends in an anterior direction towards the anterior wall of the vagina 126. To achieve this, any section of the connecting portion 206, for example the positioning portion 204, may be held to manipulate the device 200. Once this has been achieved, the user applies an upward force to the device such that the connecting portion 206 is compressed until the positioning portion 204 may be located in the securing position. Once this is achieved, the compressing force of the user may be released and the connecting portion 206 provides the necessary biasing force to retain the device 200 within the vagina 126.

Figure 3:
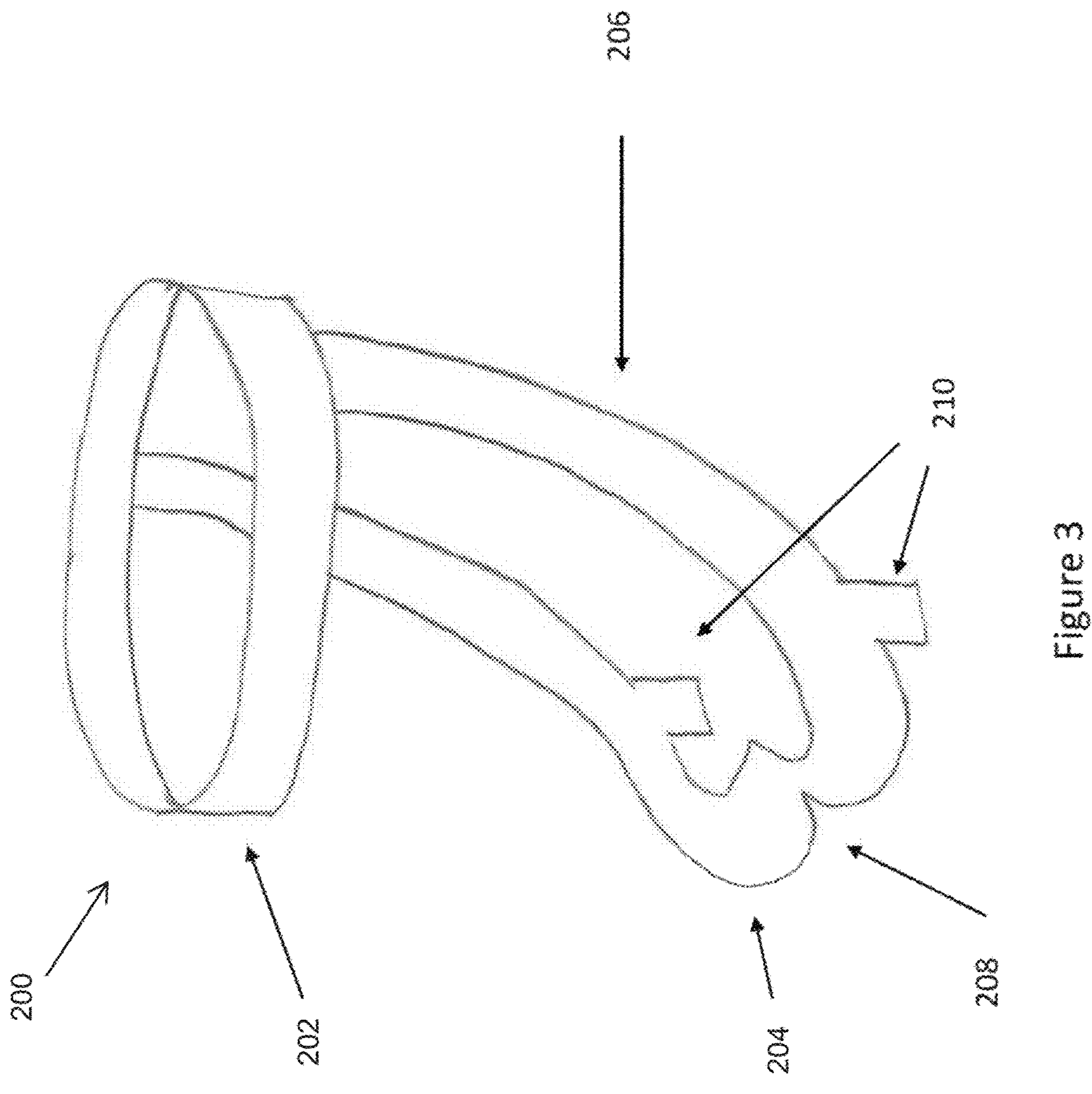
FIG. 3 illustrates a device for insertion into a vagina according to a second aspect of the present disclosure.

FIG. 3 shows a second example of the device 200. In this example, the device 200 further comprises an indentation 208 and a tab 210. The indentation 208 is located in the positioning portion 204. The indentation 208 in the positioning portion 204 is arranged to accommodate the urethra 110 when the positioning portion 204 is biased towards the pubic bone 108 and/or the top of the levator muscles 145. This insures that the device 200 is comfortable and does not affect the function of the urinary bladder 106 or urethra 110. The indentation 208 may be located in the centre of the positioning portion 204, as shown in FIG. 3. This configuration is particularly desirable to allow the indentation 208 to fit the urethra 110 easily and be positioned so that the device 200 is as comfortable as possible. When the indentation 208 is located in the centre of the positioning portion 204, the device 200 is balanced when in use, such that the weight of the device is positioned equally on either side of the urethra 110. Therefore, when the securing position is against the pubic bone 108, the weight of the device is positioned equally on either side of the pubic bone 108.

The device 200 shown in the example of FIG. 3 optionally also has tabs 210, for example two tabs 210, however there may only be one tab 210 or indeed more than two tabs 210. The tabs 210 extend from the device 200 and are useful to aid in positioning the device 200 within the vagina 126. As shown in FIG. 3, each tab 210 can be located on the positioning portion 204. Alternatively, one or more of the tabs 210 can be positioned on the connecting portion 206, or the tabs 204 can be located at the intersection between the positioning portion 204 and the connecting portion 206. The tabs 210 provide a region for the user of the device 200 to grip and manipulate the device 200 to ensure that the device 200 is correctly positioned. Furthermore, the tabs 210 can also be used to aid removal of the device 200 from the vagina 126. The user of the device 200 may also use the tabs 210 to remove the positioning portion 204 out of the securing position. The tabs 210 beneficially therefore aid insertion and removal by providing a region that can be easily accessed and gripped by the user, and may also therefore help prevent any spillages when the device 200 is used as a menstruation device.

As shown in FIG. 3, the tabs 210 have a rectangular or square shape, although they could conceivably be formed in any shape, so long as they can be gripped by the user to aid insertion and removal of the device. The tabs 210 extend downwards such that, when the device 200 is in use, they extend towards the opening of the vagina 116. The tabs 210 can be integrally formed or can be attached to the device 200 via an adhesive or other attachment means. Where the tabs 210 are integrally formed, they are made of the same material as the positioning portion 204 and/or connecting portion 206. Alternatively, in the case that the tabs 210 are attached via an adhesive or other attachment means, they could be made of a different material to the device. For example, the tabs 210 could be pieces of string.

It is desirable for the device 200 to have two tabs 210, as shown in FIG. 3. Ideally, the device 200 will have one tab 210 located on each side of the positioning portion 204 such that, when the device 200 is positioned inside the vagina 126, the device will have one tab 210 located on each side of the pubic bone 108. This configuration allows the positioning portion 204 of the device 200 to be more easily manipulated into the securing position by moving either of the tabs 210 depending on the configuration of the device 200 inside the vagina 126 after insertion.

In any of the examples described herein, the cervical ring 202 may include an inflatable portion (not shown). Such an inflatable portion may be similar to those used in endotracheal tubes. The inflatable portion is positioned on or around the circumference of the cervical ring 202. The inflatable portion can be positioned along the whole of the circumference of the cervical ring 202, or only part of it. The inflatable portion can be located on the outside, inside, or top of the cervical ring 202. The inflatable portion is used to for three main reasons. The first reason is to improve the comfort of the user, the second reason is to improve the securement of the device 200 within the vagina 126, and the third reason is to improve the seal created between the cervical ring 202 and the cervix 130. The inflatable portion may therefore be inflated from a first volume (deflated) to a second volume (inflated). The second volume is greater than the first volume, and as such the second volume causes the inflatable portion to press up against the top wall of the vagina 126 and form a seal around the cervix 130. Depending on the user and/or size of the inflatable portion, it may be possible to insert the device 200 into the vagina 126 with the inflatable portion already inflated, or it may be preferable to inflate the inflatable portion after insertion.

To achieve such an inflation, the inflatable portion also comprises a first pilot line (not shown) with a first end connected to the inflatable portion and a second end connected to a first valve (not shown). The first pilot line provides an air flow path to deliver air into the inflatable portion. Alternatively, it is also possible to have the valve directly connected to the inflatable portion.

The first valve allows air to flow in two directions; into and out of the inflatable portion. The first valve is used to control the flow of air to the inflatable portion. The first valve has an open setting and a closed setting, when the first valve is set to 'open' air can flow into and out of the inflatable portion and when the first valve is set to 'closed' air is sealed within the inflatable portion. The valve can be switched between the open and closed setting by using a twist or button, used to seal the valve. The connection of the first pilot line to the inflatable portion provides a hermetic seal. The inflatable portion is inflated when air is delivered to the inflatable portion via the first pilot line, to achieve this is the first valve is in the 'open' position and air can flow through the valve. Once the inflatable portion is sufficiently inflated, the valve is set to the 'closed' position, this traps the air inside the inflatable portion. The inflatable portion can then be deflated by, again, opening the valve and allowing the air to flow out of the inflatable portion via the first pilot line. Air can be delivered to the valve and first pilot line via a pump or syringe filled with air. For example, air can be delivered to the through the valve and first pilot line by applying pressure to a syringe filled with air. The air in the syringe is displacement by the pressure applied to the syringe and the air enters the first pilot line and, therefore, the inflatable portion. Alternatively, the inflatable portion can be self-inflating such that we the valve is in the 'open' position air is automatically delivered to the inflatable portion. As mentioned above, the device 200 may be inserted into the vagina 126 without the inflatable portion inflated and, once in position, the inflatable portion can then be inflated.

Figure 4:
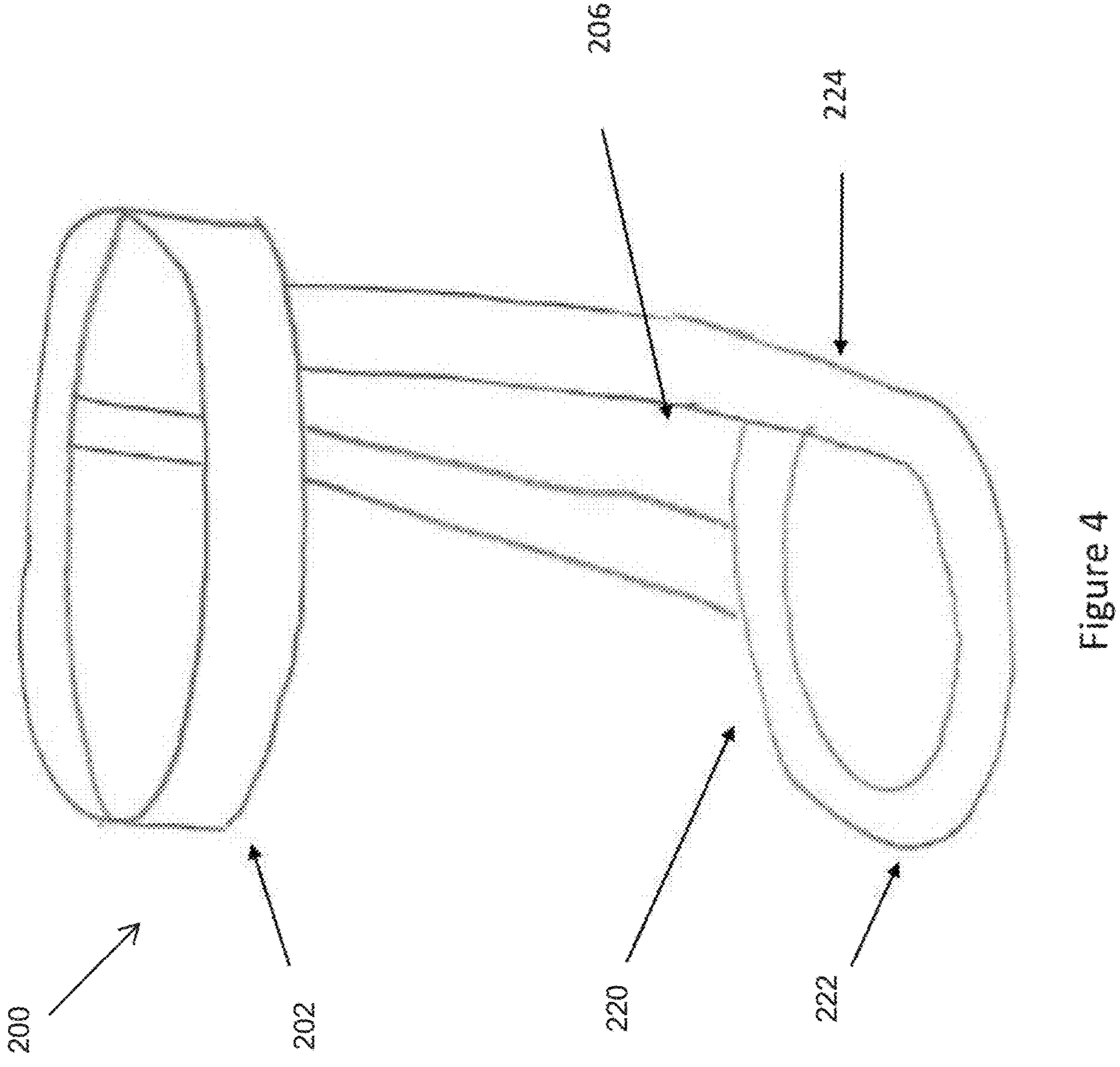
FIG. 4 illustrates a device for insertion into a vagina according to a third aspect of the present disclosure.
Figure 5:
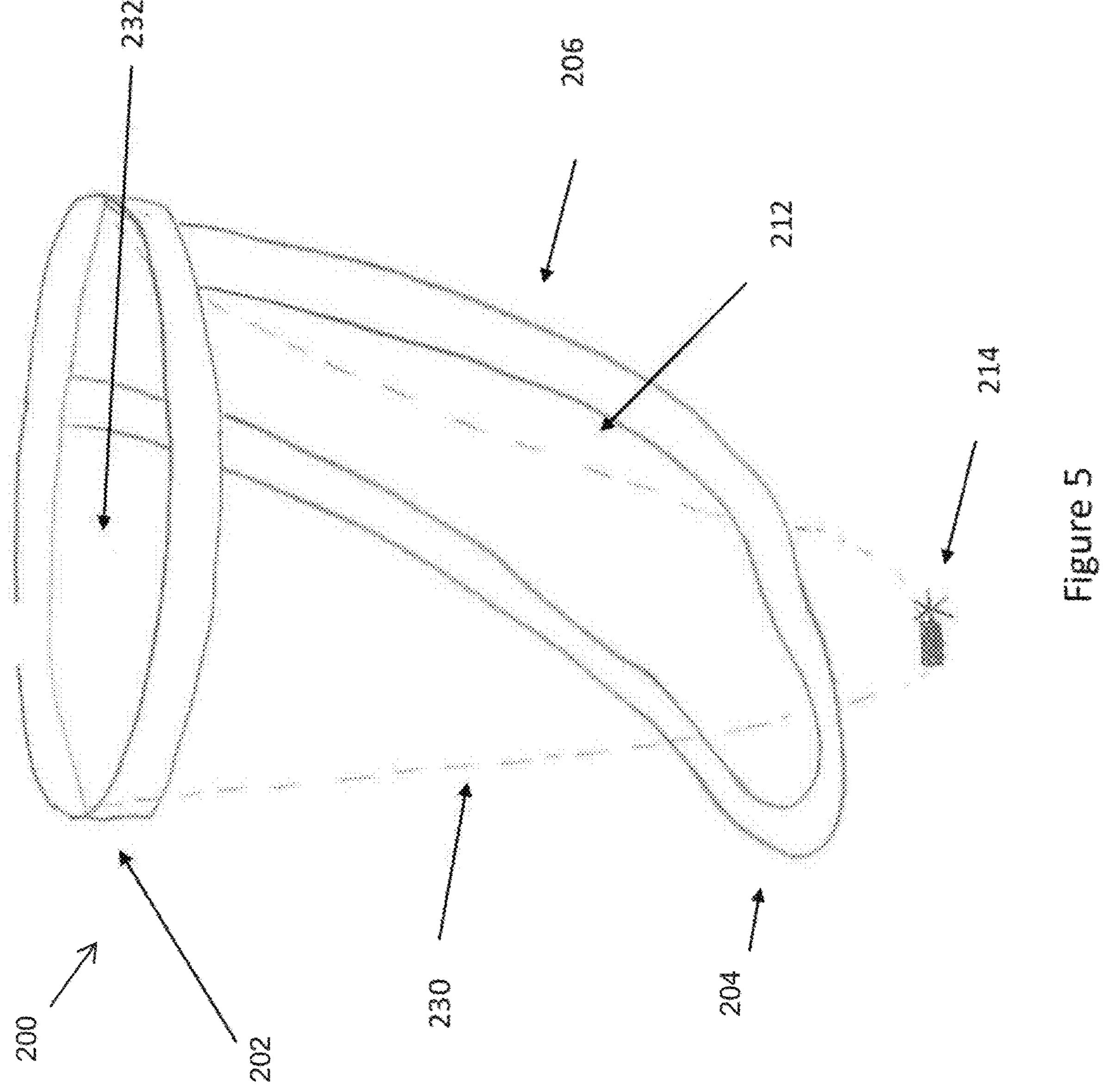
FIG. 5 illustrates a device for insertion into a vagina according to a fourth aspect of the present disclosure.

FIG. 4 shows a third example of the device 200. The device 200 shown in FIG. 5 is similar to the device 200 of FIG. 2, however the positioning portion 204 additionally comprises a positioning ring 220. The positioning ring 220 comprises an anterior end 222 and a posterior end 224. The anterior end 222 serves as the positioning portion 204 and is arranged to be locating in the securing position in the same way as previously described for the positioning portion 204. The posterior end 224 abuts against the opposite, posterior wall 124 of the vagina 126. The positioning ring 220 is elastically resilient and sized to be generally larger than the corresponding area of the vagina 126. As such, when the device 200 is inserted into the vagina 126, the positioning ring 220 compresses to accommodate the space. Due to the resilience of the positioning ring 220, the positioning ring 220 provides a force to bias the anterior end 222 into the securing position (towards the pubic bone 108 and/or levator muscles 145) and the posterior end 224 against the opposite posterior wall of the vagina 126. The positioning ring 220 therefore increases the securement of the device 200 within the vagina 126 due to the additional bias force provided.

The positioning ring 220 may have a circular shape, or alternatively, the positioning ring 220 can have an ellipse shape. The positioning ring 220 may be doughnut shaped, otherwise known as a torus shape.

The connecting portion 206 of the FIG. 4 device is connected to the cervical ring 202 via the same connections as previously described in relation to FIG. 2. In addition, the connecting portion 206 connects to the positioning ring 220 via two separate connection regions, which may be located at any points around the circumference of the positioning ring 220. Unlike the devices of FIGS. 3 and 4, the connecting portion 206 of FIG. 4 need not extend towards the anterior wall of the vagina 126, and instead may extend in any direction generally downwards. This is because the positioning ring 220 is sized and shaped to provide the necessary bias force towards the superior surface of the pubic bone and/or the top of the levator muscles 145, as previously described. Due to the resilience and shape of the connecting portion 206, once the device 200 is appropriately located within the vagina 126 (cervical ring 202 located around the cervix 130, and anterior end 222 in the securing position), the connecting portion 206 provides a biasing force to bias both the anterior end 222 down into the securing position and towards the superior surface of the pubic bone 108 and/or the top of the levator muscles 145, and the cervical ring 202 up against the uterus 132 to surround the cervix 130. This biasing force ensures that the device 200 is securely held within the vagina 126, as for the device of FIG. 2.

It may, however, be beneficial for the connecting portion 206 to be curved in the same manner as previously described for FIG. 2, to assist in providing the biasing force to bias the anterior end 222 towards the superior surface of the pubic bone 108 and/or the top of the levator muscles 145.

Although FIG. 4 shows a connecting portion 206 having two separate arms (each arm extending between the positioning ring 220 and the cervical ring 202), the connecting portion 206 may only have one arm extending between the positioning ring 220 and the cervical ring 202.

The devices 200, as described in any of the examples herein, can be used to treat pelvic organ prolapse, similar to the treatment provided by a vaginal or ring pessary. Pelvic organ prolapse is when one or more of the organs in the pelvis slips down from its normal position and bulges into the vagina 126. Pelvic organ prolapse happens when the group of muscles and tissues that normally support the pelvic organs, called the pelvic floor, becomes weakened and can't hold the organs in place firmly. The device 200 may therefore be inserted into the vagina 126 and left in place to support the vaginal walls and pelvic organs. Once inserted, the positioning portion 204 (or anterior end 222 serving thereas) pushes against the anterior wall 123 of the vagina 126 and the cervical ring 202 pushes against the posterior wall 124 of the vagina 126, as previously described. The cervical ring 202 therefore pushes upwards against the uterus 132 to hold the uterus 132 and prevent prolapse. The cervical ring 202 also pushes the anterior 123, posterior 124 and side walls of the vagina outwards. When used in this way, the device 200 can ease the symptoms of moderate or severe prolapses and can be an alternative option to having surgery. The device 200 can also be used to allow pregnancy in the future, by supporting the walls of the vagina 126. When used to treat pelvic organ prolapse, the device 200 may need to be removed, cleaned and replaced regularly.

FIG. 5 shows a fourth example of the device 200. This example is the same as the example of FIG. 2, but further comprises a bag 212. The bag 212 is connected to the cervical ring 202 of the device 200. The bag 212 is connected to and/or hangs from the circumference of the cervical ring 202 e.g. on the top, bottom, inside or outside of the cervical ring 202. The bag 212 extends from the cervical ring 202 towards the opening 116 of the vagina, when in use. The bag 212 is formed of a bag wall 230 and a bag opening 232. The bag 212 may be made from a non-allergenic material such as medical grade silicon. The bag opening 232 corresponds to the circumference of the cervical ring 202.

As shown in FIG. 5, the bag may be cone-shaped, such that the circle forming the base of the cone corresponds to the opening of the bag, and the vertex of the bag/cone is located at the nearest point to the opening of the vagina 116, when in use. The opening of the bag 232 is circular and has a circumference that corresponds to the circumference of the cervical ring 202. Where the device 200 has a positioning portion 206 comprising two arms, the bag 212 is positioned such that it falls between the two arms as shown in FIG. 5. This ensures that the bag 212 does not interfere with the positioning and security of the device 200. In this way, the device 200, may be used to treat pelvic organ prolapse and also used as a device 200 for use during menstruation.

As one option, the bag 212 can be permanently connected to the device 200. The bag 212 can be connected to the cervical ring 202 by a glue or other adhesive. The opening of the bag 232 is attached to the circumference of the cervical ring 202. The glue or adhesive is located along the cervical ring and opening of the bag 232, the glue can be placed at intervals or along the entire length of the circumference of the cervical ring 202 and the circumference of the opening of the bag 232. Alternatively, bag 212 can be manufactured as an integral part of the cervical ring 202.

The bag 212 is used to collect tissue and blood shed from the uterus 132 during menstruation. As would be understood, blood exits the uterus 132 through the cervix 130 and is collected in the bag 212. As the cervical ring 202, and the bag 212 attached thereto, surround the cervix 130, all blood is collected in the bag 212. The device 200 must therefore be regularly removed to drain the blood collected in the bag 212, and to allow cleaning of the device 200. The bag 212 keeps the walls of the vagina 126 dry, clean and free from blood. This provides a hygienic way to manage periods and prevents infection, such as toxic shock syndrome.

As mentioned, the device 200 is removable and can be removed from the vagina 126, cleaned and reused. It is therefore desirable to have a reusable product to avoid having to use a new product each month. A reusable device is of course also beneficial from an environmental point of view. Environmental benefits include reduced water pollution and reduced handling costs, especially in less developed countries with less sophisticated waste disposal systems.

The bag 212 further comprises a valve 214. The valve 214 is located at the bottom of the bag 212 and can be used as an outlet to drain blood from the bag 212 whilst the device 200 is still located inside the vagina 126. Beneficially, the bag 212 may be cone shaped such that the blood collects and flows more easily out of the valve 214. Such a cone shaped bag 212 is connected to the cervical ring 202 of the device 200. The valve 214 is located at a point of the cone shaped bag 212 distal from the cervical ring 202. During menstruation, blood and other tissue collects into the bag 212 from the cervix 130. The valve 214, and optionally at least some of the bag 212, can be pulled out of the vagina 126 while the device 200 is still inserted to allow the user of the device 200 to release the blood/tissue stored in the bag 212 by opening the valve 214. Thus, any contents stored within the bag 212 may be released in a controllable and clean way, via operation of the valve 214. After the bag 212 has been emptied, the user may close the valve 214 for further use. Depending on the particular user and dimensions of the bag 212/valve 214, the bag 212 and/or valve 214 may be returned inside the vagina 126.

Optionally, the bag 212 may be removable from the device 200. In this case, the bag 212 is connected the cervical ring 202 via an attachment means, such as via clips or an adhesive. Such an adhesive may be reusable. Any suitable attachment means may be used, as long as the attachment of the bag 212 to the cervical ring 202 provides a sufficient seal. In the case of the bag 212 being reusable, the bag 212 may be removed at any point for cleaning and/or replacement of a new bag 212 to be attached to the cervical ring 202.

Optionally, the bag 212 itself, like the inflatable portion of the cervical ring 202 previously described, may also or instead include an its own inflatable portion (not shown). The inflatable portion may provide a secure seal to seal the end of the bag 212 against the walls of the vagina. Therefore, any blood/tissue exiting the cervix 130 enters the bag 212 without entering any other region of the vagina 126. During menstruation, when the bag 212 is also used, this ensures that blood flows out of the cervix 130 and into the bag 212. The inflatable portion therefore helps to keep the walls of the vagina clean and dry during menstruation.

Optionally, the device 200 may also comprise a washing tube (not shown). The washing tube can be located on, in or around the cervical ring 202, the inflatable portion or the bag 212. The washing tube has at least one first opening therein for allowing fluid, such as water, to exit the washing tube. When water enters the washing tube, the at least first one opening therefore provides an exit hole for water to exit the washing tube and impinge on the interior of the vagina 126. The at least one first opening is therefore located facing outwards from the centre of the cervical ring 202. There may be multiple first openings located around the washing tube.

To achieve a washing effect, the washing tube comprises a second pilot line (not shown). The second pilot line has a first end connected to the washing tube and a second end connected to a second valve. The second pilot line provides a fluid flow path to deliver water from outside the device into the washing tube such that, when water is supplied to the second pilot line, water is delivered to the interior of the vagina 126 via the second pilot line, the washing tube and the at least one opening. As such, water may be delivered to the walls of the vagina 126 to remove any residual blood/tissue. The delivery of water to the second pilot line may be achieved by connecting a source of water to the second pilot line and opening the second valve. Such a source of water may be deformable such that it may be squeezed by the user to force water into the washing tube via the second pilot line. After use, the second valve may be closed. Indeed, the source of water may be connected to the second pilot line in a permanent or temporary manner.

The washing tube may further comprise at least one second opening (not shown). Unlike the at least one first opening, the at least one second opening is arranged to deliver water to the interior of the bag 212. The purpose of the at least one second opening is therefore to allow water to enter the inside of the bag 212 to clean the bag. Accordingly, supplying water to the second pilot line therefore provides water to both the inside of the bag 212 and the outside of the bag 212. A user may then, before or after the water is supplied, open the valve 214 to allow water to flow through the bag 212 and exit the bag 212.

Although the above example includes at least one first opening and at least one second opening, the device 200 may include only one of the at least one first opening and the at least one second opening. In other words, the device 200 may allow only washing of the inside of the bag 212, only washing of the area outside of the bag 212, or indeed both.

The example shown in FIG. 5 may also include one or all of the indentation 208, tabs 210, bag 212, inflatable portion or washing tube as previously described.

The device 200 may be made of materials that can be washed in boiling water without causing damage to the device 200. Such materials may therefore be sterilised for future use.

The device has been described for use as a treatment of pelvic organ prolapse and for use during menstruation. The device can be used for either purpose or for both purposes simultaneously.

Features of the above aspects can be combined in any suitable manner. It will be understood that the above description is of specific examples only and that many modifications and alterations will be within the skilled person's reach and are intended to be covered by the scope of the claims.

The invention claimed is:

1. A device for insertion into a vagina, the device comprising:

a cervical ring configured to surround the cervix;

a positioning portion configured to abut against a securing position along an interior wall of the vagina;

an elastically resilient connecting portion connecting the cervical ring and the positioning portion, wherein the elastically resilient connecting portion is configured such that, when the device is positioned inside the vagina, the positioning portion is biased against the securing position; and a bag connected to the cervical ring, and the bag further comprises a valve, wherein the valve is configured for draining blood from the bag when the device is in use.

2. The device of claim 1 wherein the bag is configured to be removable from the cervical ring.

3. The device of claim 1 further comprising a washing tube, wherein the washing tube comprises a first opening configured to deliver water to the walls of the vagina, wherein the washing tube is located in the wall of the bag.

4. The device of claim 3 wherein the washing tube comprises a second pilot line with a first end connected to the washing tube and a second end connected to a second valve, wherein the second pilot line is configured to deliver water to the washing tube.

5. The device of claim 3 wherein the washing tube comprises a second opening configured to deliver water to the inside of the bag.

6. The device of claim 4 wherein the first pilot line and second pilot line are removable.

7. The device of claim 1 wherein the positioning portion further comprises an indentation configured to accommodate a urethra when the device is positioned inside the vagina.

8. The device of claim 7 wherein the indentation is located in the center of the positioning portion.

9. The device of claim 1 further comprises at least one tab protruding from the device.

10. The device of claim 9 wherein the at least one tab extends downwards such that, when the device is positioned inside the vagina, the at least one tabs extends towards the opening of the vagina.

11. The device of claim 9 wherein the device has at least two tabs, and one tab located on each side of the positioning portion such that, when the device is positioned inside the vagina, the device will have one tab located on each side of the pubic bone.

12. The device of claim 1 wherein the cervical ring further comprises an inflatable portion.

13. The device of claim 12 wherein the inflatable portion is positioned on the circumference of the cervical ring.

14. The device of claim 12 further comprising a washing tube, wherein the washing tube comprises a first opening configured to deliver water to the walls of the vagina.

15. The device of claim 14 wherein the washing tube is located in the inflatable portion of the device.

16. The device of claim 14 wherein the washing tube is located in the cervical ring.

17. The device of claim 1 wherein the inflatable portion comprises a first pilot line with a first end connected to the inflatable portion and a second end connected to a first valve, wherein the first pilot line is configured to provide air to inflate the inflatable portion.

18. The device of claim 1 wherein the connecting portion is curved and the gradient of the curve of the connecting portion increases as distance from the cervical ring increases.

* * * * *